US012630813B2

(12) United States Patent
Sun et al.

(10) Patent No.: US 12,630,813 B2
(45) Date of Patent: May 19, 2026

(54) TEV PROTEASE WITH DUAL AFFINITY TAGS

(71) Applicant: AbClonal Science, Inc., Woburn, MA (US)

(72) Inventors: Dapeng Sun, Lexington, MA (US); Zhenyu Zhu, Lynnfield, MA (US); Aine Quimby, Newburyport, MA (US)

(73) Assignee: ABCLONAL SCIENCE, INC., Woburn, MA (US)

( * ) Notice: Subject to any disclaimer, the term of this patent is extended or adjusted under 35 U.S.C. 154(b) by 296 days.

(21) Appl. No.: 18/429,347

(22) Filed: Jan. 31, 2024

(65) Prior Publication Data

US 2024/0392276 A1 Nov. 28, 2024

Related U.S. Application Data

(60) Provisional application No. 63/442,788, filed on Feb. 2, 2023.

(51) Int. Cl.
*C12N 9/64* (2006.01)

(52) U.S. Cl.
CPC ........ *C12N 9/6472* (2013.01); *C07K 2319/21* (2013.01); *C12Y 304/22044* (2013.01)

(58) Field of Classification Search
CPC ...... C12N 9/6472; C12N 9/506; C12N 11/02; C12N 11/14; C07K 2319/21; C07K 2319/20; C07K 2319/50; C07K 2319/02; C12Y 304/22044; C12P 21/06
See application file for complete search history.

(56) References Cited

U.S. PATENT DOCUMENTS

| | | | |
|---|---|---|---|
| 10,920,202 B1 | 2/2021 | Zhu et al. | |
| 10,947,518 B1 | 3/2021 | Zhu et al. | |
| 11,020,474 B1 | 6/2021 | Xiang et al. | |
| 12,358,947 B2 * | 7/2025 | Stikeleather | C07K 1/22 |
| 2020/0283825 A1 | 9/2020 | Zhu et al. | |
| 2020/0291455 A1 | 9/2020 | Zhu et al. | |
| 2020/0362320 A1 | 11/2020 | Zhu et al. | |
| 2021/0079365 A1 | 3/2021 | Zhu et al. | |
| 2021/0087550 A1 | 3/2021 | Zhu et al. | |
| 2021/0171925 A1 | 6/2021 | Zhu et al. | |

| | | | |
|---|---|---|---|
| 2021/0380655 A1 * | 12/2021 | Grinstaff | C12N 5/10 |
| 2021/0403537 A1 | 12/2021 | Xiang et al. | |
| 2022/0064266 A1 | 3/2022 | Xiang et al. | |
| 2022/0106576 A1 | 4/2022 | Zhu et al. | |
| 2023/0033390 A1 | 2/2023 | Xiang | |
| 2023/0094503 A1 | 3/2023 | Zhu et al. | |
| 2023/0111383 A1 | 4/2023 | Zhu et al. | |
| 2023/0212550 A1 | 7/2023 | Zhu et al. | |
| 2023/0257425 A1 * | 8/2023 | Kwon | C07K 14/005 |
| | | | 424/192.1 |
| 2023/0265412 A1 | 8/2023 | Zhu et al. | |
| 2023/0295707 A1 | 9/2023 | Zhu et al. | |
| 2024/0052326 A1 | 2/2024 | Zhu et al. | |
| 2024/0067951 A1 | 2/2024 | DiCicco et al. | |
| 2024/0124854 A1 | 4/2024 | Zhu et al. | |
| 2024/0247246 A1 | 7/2024 | Sun et al. | |
| 2024/0279626 A1 | 8/2024 | Sun et al. | |
| 2024/0392264 A1 | 11/2024 | Zhu et al. | |
| 2024/0392267 A1 | 11/2024 | Zhu et al. | |
| 2024/0392276 A1 | 11/2024 | Sun et al. | |
| 2024/0392336 A1 | 11/2024 | Sun et al. | |
| 2025/0051739 A1 | 2/2025 | Zhu et al. | |
| 2025/0223574 A1 | 7/2025 | Zhu et al. | |
| 2025/0236860 A1 | 7/2025 | Sun et al. | |

OTHER PUBLICATIONS

Chung et al., The Use of Inulinase Pre-Pro Leader Peptide for Secretion of Heterologous Proteins in *Saccharomyces cerevisiae*. Biotechnol. Lett., 1996, vol. 18(6): 627-632. (Year: 1996).*
Stamsas et al., CHIC, a new tandem affinity tag for the protein purification toolbox . J. Mocrobiol., Methods., 2013, vol. 92: 59-63 (Year: 2013).*

* cited by examiner

*Primary Examiner* — Ganapathirama Raghu
(74) *Attorney, Agent, or Firm* — Eric P. Mirabel

(57) ABSTRACT

Disclosed is using a TEV protease (wild type or mutant) suited for removal from a reaction mixture, wherein the TEV protease displays a dual affinity tag including a chitin binding domain (CBD) tag and a histidine tag, preferably where the CBD tag precedes the N-terminus of the protease and the CBD tag is preceded by the histidine tag, which is preferably a 6-mer histidine tag; and optionally further including linkers, preferably Gly-Ser linkers, and more preferably a 6-mer Gly-Ser linker, between the tags. A linker, also preferably a Gly-Ser linker, can also follow the CBD tag and precede the protease portion. In certain embodiments, no such linkers are present and in other embodiments, only one such linker is present.

13 Claims, 3 Drawing Sheets

Specification includes a Sequence Listing.

FIG. 1

| 6x His | CBD | TEV protease |

TEV PROTEASE WITH DUAL AFFINITY TAGS

The instant application contains a Sequence Listing which has been submitted electronically in XML file format and is hereby incorporated by reference in its entirety. Said XML copy, was created on Feb. 14, 2024, is named 442788.xml, and is 12,798 bytes in size.

BACKGROUND

Protein proteases are a group of enzymes that cleave proteins and peptides. Proteases are widely used in industry and biotechnology, including production of Klenow fragments, peptide synthesis, digestion of unwanted proteins during nucleic acid purification, cell culturing and tissue dissociation.

The protease trypsin cleaves peptides at specific sites. Proteinase K cleaves non-specifically. TEV Protease is a widely used cysteine protease derived from Tobacco Etch Virus that recognizes the cleavage site between Q and S in the protein sequence E-N-L-Y-F-Q/S (SEQ ID NO: v 8) and cleaves there with high efficiency. It can also recognize and cleave between Q and X in the sequence E-N-L-Y-F-Q/X (SEQ ID NO: 9), where X can be any of the amino acids G, A, M, C, or H.

Chitin binding domain (CBD) is a polypeptide which specifically binds to N-acetyl glucosamine. CBD is derived from the small domain of the chitinase A1 gene of *Bacillus circulans*. CBD binding affinity is so high as to be nearly irreversible, making it useful in tagging proteins for purification purposes. The CBD binds tightly to chitin, which is a poly N-acetyl glucosamine and one of the most common polymers from nature. Chitin exists in the shells of all crustaceans, the skeletons of insects, and many fungi, algae, and yeast. Chitin is commercially available as resin, as chitin beads, or in chitin magnetic beads (New England Biolabs, Ipswich, MA,). Proteins expressed with the CBD-tag, or as a fusion protein in which the CBD is fused to the target protein, can be subjected to purification using chitin beads, or other bound chitin. Proteins immobilized to chitin resin or beads via CBD-tags can be separated from crude cell lysate through affinity purification protocols. Purified protein is eluted from the CBD via chemically inducing internal cleavage between the tag and the fused protein.

Another commonly used tag in affinity chromatography is the poly-histidine tag (His-tag), which involves the addition of an uninterrupted string of about four to ten histidine residues to the N- or C-terminus of a target protein. His-tagged proteins can bind to the immobilized metal ions in a carrier such as a resin or magnetic bead. Bound protein can be eluted after purification using increasing concentrations of imidazole, which competes with the target protein for binding with the metal ions, displacing purified protein into solution for recovery.

Methionine is the typical starting amino acid for every whole protein. A protein can be engineered to present an N-terminus amino acid tag such that the starting methionine occurs immediately after TEV cleavage site, like: E-N-L-Y-F-Q/M (SEQ ID NO: 10). TEV protease can cleave off the amino acid tag cleanly, leaving an intact protein without any additional unwanted N-terminal amino acid residues. After digestion, however, TEV is commonly removed because a poly-histidine tag fused to TEV was part of a TEV fusion protein. The TEV fusion protein can be removed by binding, through the poly-histidine tag, to nickel beads or nickel magnetic beads. However, if the target protein also has a His-tag, or if the target also binds to nickel beads by virtue of high intrinsic histidine content, it is desirable to have another method to remove TEV protease after it performs the desired cleavage reaction.

To date, a combination of the CBD-tag in conjunction with a His-tag has not been used to purify TEV protease in a protocol that retains both the His-tag and the CBD-tag after purification, and uses bound nickel and/or chitin for purification, by binding respectively to the poly-histidine tag or the CBD tag. Engineering TEV protease to display both a 6-mer His-tag and a CBD-tag broadens the field of application to allow purification of a wider target range (including targets with a high histidine content), compared to TEV protease with only a His-tag.

SUMMARY

The invention relates to a TEV protease (wild type or mutant) displaying a dual affinity tag including a chitin binding domain (CBD) tag and a histidine tag, preferably where the CBD tag precedes the N-terminus of the protease and the CBD tag is preceded by the histidine tag, which is preferably a 6-mer histidine tag; and optionally further including linkers, preferably Gly-Ser linkers, and more preferably a 6-mer Gly-Ser linker, between the tags. A linker, also preferably a Gly-Ser linker, can also follow the CBD tag and precede the protease portion. In certain embodiments, no such linkers are present and in other embodiments, only one such linker is present.

The invention further includes the amino acid sequences of fusion proteins where: a wild-type TEV protease displaying a dual affinity tag is arranged such that a chitin binding domain (CBD) tag precedes the N-terminus of the protease, and the CBD tag is preceded by a His-tag (preferably a 6-mer histidine tag) and preferably Gly-Ser linkers (preferably a 6-mer Gly-Ser linker) are between the tags; as well as the amino acid sequences of such fusion proteins where the TEV protease in the fusion protein is a mutant TEV protease whose amino acid sequence only has conservative substitutions such that it has at least 70%, 80%, 90%, 95%, 96%, 97%, 98% or 99% identity to the wild-type TEV protease mutant amino acid sequence (such sequences of mutant TEV protease are hereinafter referred to as "Variant Sequences").

The invention further includes the RNA or DNA (collectively the "Degenerate Nucleic Acid Sequences") encoding any of the fusion proteins, including fusion proteins containing the Variant Sequences (collectively the "Fusion Proteins" or individually, a "Fusion Protein").

The invention further includes vectors incorporating any Degenerate Nucleic Acid Sequences; and cells transformed with any such vectors or Degenerate Nucleic Acid Sequences and capable of expressing any of the Fusion Proteins, including Fusion Proteins containing the Variant Sequences.

The invention further includes a composition or a kit encoding any of the Fusion Proteins, or including any of the Degenerate Nucleic Acid Sequences, or vectors incorporating such Degenerate Nucleic Acid Sequences. The invention also includes a process of cleaving a target protein using one more of the Fusion Proteins in the reaction mixture designed to cleave the target protein.

The invention further includes using a Fusion Protein to remove TEV protease from reaction mixtures, including reaction mixtures where the targets or other products in the reaction mixture have a high histidine content.

Additional aspects and advantages of the present disclosure will become apparent to those skilled in this art from the following detailed description and drawings, wherein only illustrative embodiments of the present disclosure are shown and described. The present disclosure is capable of other and different embodiments, and several details are capable of modifications in various obvious respects, and its several details are capable of modifications in various obvious respects, all without departing from the disclosure. Accordingly, the descriptions, and examples in this summary are intended for purposes of illustration only and are not intended to limit the scope of the present disclosure.

BRIEF DESCRIPTION OF THE FIGURES

FIG. 1: The construction scheme of His-CBD-TEV, starting from the N-terminus, is: a 6-mer His-tag, followed by a CBD-tag, and then the TEV protease. Linkers are not shown, but, if present, would preferably be between the His tag and the CBD tag and/or after the CBD tag and before the protease.

DETAILED DESCRIPTION

Figure 2:
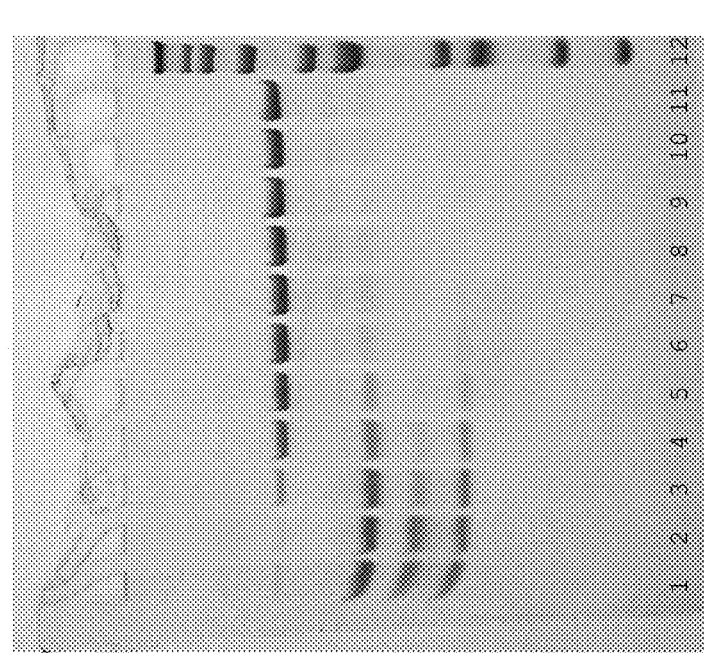
FIG. 2: Bis-tris protein gel showing 1 µg of eGFP displaying an MBP tag connected with a TEV cleavage site (labeled MBP-TEVsite-eGFP) digested by His-CBD-TEV in a 2-fold serial dilution at 30° C. for 30 minutes in 1×TEV Protease Buffer (New England Biolabs, Inc) with added imidazole. Lanes 1 to 11 show the digestion of MBP-TEVsite-eGFP by His-CBD-TEV protease, which is serially diluted 2-fold from 0.32 ug in lane one into decreasing concentrations through lane 11. For each digestion lane, four major bands are visible: the top band is full-length eCFP with the MBP attached via a TEV site; the next band below is the MBP-tag after being cleaved from the eGFP protein; the second-lowest band is His-CBD-TEV protease, diminishing as protease concentration decreases from left to right; and, the lowest band represents eGFP after cleavage from the MBP tag at the TEV site. Lane 12 is the ColorMixed Protein Marker 180 (10-180 kDa) (ABclonal, Woburn MA).

The embodiments herein and the various features and advantageous details thereof are explained more fully with reference to the non-limiting embodiments that are illustrated in the accompanying drawings and the following description. Numerous variations, changes, and substitutions may occur to those skilled in the art without departing from the invention. It should be understood that various alternatives to the embodiments of the present disclosure herein may be employed.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

The articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

The term "biologically active fragment" refers to any fragment, derivative, homolog or analog of a TEV protease mutant that possesses in vivo or in vitro activity that is characteristic of that biomolecule; including, for example, protease activity. In some embodiments, the biologically active fragment, derivative, homolog or analog of the mutant TEV protease possesses any degree of the biological activity of the mutant TEV protease in any in vivo or in vitro assay of interest.

In some embodiments, the biologically active fragment can optionally include any number of contiguous amino acid residues of the mutant TEV protease. The invention also includes the polynucleotides encoding any such biologically active fragment.

Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

The terms "mutant TEV protease of the invention" and "mutant TEV protease" when used in this Detailed Description section refer to, depending on the context, collectively or individually, the mutants exhibiting protease activity and/or mutants having Variant Sequences and/or Degenerate Nucleic Acid Sequences, as those terms are defined in the Summary section. The term "Fusion Protein" in this Detailed Description section refer to the use of that term the Summary section.

"Naturally-occurring" or "wild-type" refers to the form found in nature. For example, a naturally occurring or wild-type polypeptide or polynucleotide sequence is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

Making Fusion Proteins

The Fusion Proteins of the invention can be expressed in any suitable host system, including a bacterial, yeast, fungal, baculovirus, plant or mammalian host cell. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75:3727-3731), as well as the tac promoter (DeBoer et al., 1983, Proc. Natl Acad. Sci. USA 80:21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

For baculovirus expression, insect cell lines derived from Lepidopterans (moths and butterflies), such as *Spodoptera frugiperda*, are used as host. Gene expression is under the control of a strong promoter, e.g., pPolh.

Plant expression vectors are based on the Ti plasmid of *Agrobacterium tumefaciens*, or on the tobacco mosaic virus (TMV), potato virus X, or the cowpea mosaic virus. A commonly used constitutive promoter in plant expression vectors is the cauliflower mosaic virus (CaMV) 35S promoter.

For mammalian expression, cultured mammalian cell lines such as the Chinese hamster ovary (CHO), COS, including human cell lines such as HEK and HeLa may be used to produce the Fusion Proteins. Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoters, such as the elongation factor (EF)-1 promoter, are also known.

The control sequence for the expression may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Terminators for insect, plant and mammalian host cells are also well known.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57:109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Signal peptides for other host cell systems are also well known.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the Fusion Proteins relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Regulatory systems for other host cells are also well known.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide of the present invention would be operably linked with the regulatory sequence.

Another embodiment includes a recombinant expression vector comprising a polynucleotide encoding an engineered mutant Fusion Protein, and one or more expression regulating regions such as a promoter and a terminator, and a replication origin, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the Fusion Protein at such sites. Alternatively, the nucleic acid sequences of the Fusion Protein may be expressed by inserting the nucleic acid sequences or a nucleic acid construct comprising the sequences into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the Fusion Protein polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector herein preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Selectable markers for insect, plant and mammalian cells are also well known.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination. Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAM31 permitting replication in *Bacillus*. Examples of origins of replication for use in a yeast host cell are the 2 micron origins of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proc Natl Acad Sci. USA 75:1433).

More than one copy of a nucleic acid sequence of the Fusion Protein may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Expression vectors for the Fusion Protein polynucleotide are commercially available. Suitable commercial expression vectors include p3×FLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

Suitable host cells for expression of a polynucleotide encoding the Fusion Proteins, are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the Fusion Proteins may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to the skilled artisan.

Polynucleotides encoding the Fusion Proteins can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., and Operon Technologies Inc., Alameda, Calif.

Engineered the Fusion Proteins expressed in a host cell can be recovered from the cells and or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the Fusion Proteins include, among others, reverse phase chromatography high performance liquid chromatography, ion exchange chromatography, gel electrophoresis, and affinity chromatography. Conditions for purification will depend, in part, on factors such as net charge, hydrophobicity, hydrophilicity, molecular weight, molecular shape, and will be apparent to those having skill in the art.

In some embodiments, affinity techniques may be used to isolate the Fusion Proteins. For affinity chromatography purification, any antibody which specifically binds the Fusion Proteins may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Figure 1:
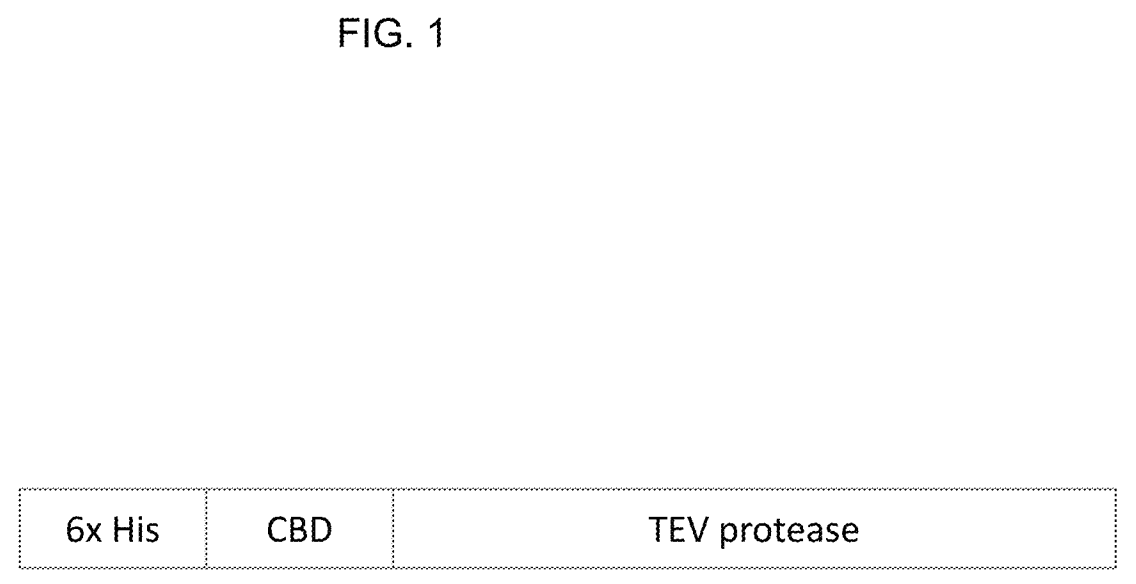

The TEV in the Fusion Proteins may be wild type or one of any of several functional mutants. The TEV mutant used in the experiments described here is the TEV mutant shown in the patent application number CN201010204707A (incorporated by reference) that bears the following mutations: T17S/L56V/N68D/I77V/S135G. The DNA sequence in SEQ ID NO: 1 encodes the protein in FIG. 1, where a 6-mer His-tag is followed by a CBD-tag, followed by the N-terminus of TEV protease. Linkers including Gly-Ser residues, including GSGSSG (SEQ ID NO: 7), may be used after either or both tags in some embodiments.

```
                                              SEQ ID NO: 1
ATGAAAATCCATCACCATCATCATCATGGGTCAGGGAGTTCCGGT

TTGACAACGAACCCGGGGGTGAGTGCTTGGCAGGTGAACACAGCG

TACACCGCTGGTCAGCTGGTGACTTACAATGGTAAAACCTACAAA

TGCCTGCAACCACACACTTCACTGGCTGGATGGGAGCCAAGCAAT

GTCCCGGCACTTTGGCAGTTACAGGGGTCTGGTAGCTCGGGAGAA

TCCCTGTTTAAAGGGCCACGTGATTATAACCCGATCTCCTCTAGT

ATATGTCACCTCACAAACGAATCCGATGGACATACCACCAGTCTT

TATGGGATTGGCTTTGGTCCGTTTATAATCACCAACAAACATCTG

TTCCGCCGCAACAATGGGACCCTGGTTGTACAATCACTGCACGGT

GTTTTCAAAGTAAAAGATACGACCACACTGCAGCAGCATTTAGTT

GATGGGCGGGACATGATAATCATTCGCATGCCAAAGGATTTTCCA

CCATTTCCACAGAAACTGAAGTTCCGCGAACCACAACGTGAGGAA

CGCATTTGTCTTGTGACGACTAATTTCCAGACCAAATCAATGAGT

TCTATGGTTAGTGATACCTCGTGTACCTTCCCGAGCGGTGATGGG

ATTTTCTGGAAACATTGGATTCAGACAAAAGATGGACAGTGCGGT

TCCCCGTTGGTATCCACAAGAGACGGTTTTATAGTTGGTATTCAT

TCTGCATCCAATTTTACCAATACAAACAACTACTTCACATCAGTT

CCGAAGAACTTTATGGAACTGTTAACTAATCAGGAGGCCCAGCAG

TGGGTATCAGGGTGGCGATTGAACGCCGACAGTGTTCTGTGGGGC

GGGCATAAAGTGTTTATGTCTAAACCGGAAGAACCTTTTCAGCCG

GTTAAAGAAGCCACTCAGTTAATGAACTGA.
```

The single underlined portion of SEQ ID NO: 1 encodes the 6-mer His-tag followed by a linker. The double-underlined part of the sequence encodes the CBD followed by another linker.

The DNA in SEQ ID NO: 1 encodes the protein without the MKI leader sequence, which is the first three amino acids in SEQ ID NO: 2:

```
MKIHHHHHHGSGSSGLTTNPGVSAWQVNTAYTAGQLVTYNGKTYK

CLQPHTSLAGWEPSNVPALWQLQGSGSSGESLFKGPRDYNPISSS

ICHLTNESDGHTTSLYGIGFGPFIITNKHLFRRNNGTLVVQSLHG

VFKVKDTTTLQQHLVDGRDMIIIRMPKDFPPFPQKLKFREPQREE

RICLVTTNFQTKSMSSMVSDTSCTFPSGDGIFWKHWIQTKDGQCG

SPLVSTRDGFIVGIHSASNFTNTNNYFTSVPKNFMELLTNQEAQQ

WVSGWRLNADSVLWGGHKVFMSKPEEPFQPVKEATQLMN
```

In SEQ ID NO: 2, the N-terminal MKI is followed by the 6-mer His tag, followed by a 6-mer Gly-Ser linker (single underlined in SEQ ID NO: 2), followed by the CBD-tag which is followed by a 6-mer Gly-Ser linker (double underlined in SEQ ID NO: 2), followed by the TEV protease.

The Fusion Protein is therefore His-CBD-TEV, with a 3-mer leader as shown in SEQ ID NO: 2 and schematically in FIG. 1, and optionally with linkers. The 3-mer N-terminal MKI tag preceding the His-CBD-TEV is cleaved off after expression. His-CBD-TEV as shown was expressed in C2566 (New England Biolabs, MA) *E. coli* competent cells with the plasmid construct as a kanamycin resistant pBAD vector. The enzyme was purified from cellular lysate using the 6-mer His-tag.

Example I

His-CBD-TEV activity was confirmed by digestion of eGFP (enhanced green fluorescent protein) with an MBP-tag connected to the protein via an engineered TEV site (SEQ ID NO: 4, below in Appendix I). A protein gel showing the results of this digestion over a serial dilution of His-CBD-TEV is shown in FIG. 2. In the presence of His-CBD-TEV, MBP-TEVsite-eGFP is cleaved into the MBP tag (43 kDa) and eGFP (33 kDa), showing that His-CBD-TEV has specific protease activity.

Figure 3:
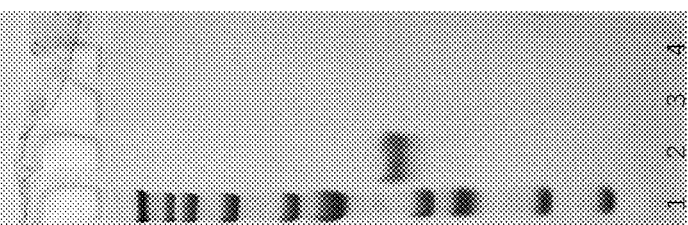
FIG. 3: Bis-tris protein gel of TEV protease with the CBD/6-mer His tag, confirming the binding capability to nickel magnetic beads or chitin magnetic beads. Lane 1 is the ColorMixed Protein Marker 180 (10-180 kDa) protein marker (ABclonal, Woburn MA). Lane 2 is 1.23 µg purified His-CBD-TEV protease. Lane 3 shows a sample containing His-CBD-TEV protease after incubation with 10 µl nickel magnetic beads. Lane 4 is the same sample after incubation with 10 µl of chitin magnetic beads.

Successful binding of His-CBD-TEV to nickel magnetic beads (Beaver, China) or chitin magnetic beads (New England Biolabs, Ipswich) is shown in FIG. 3. This protein gel of His-CBD-TEV samples after magnetic bead incubation shows His-CBD-TEV can be removed successfully using either of the added tags in the fusion protein for pulldown.

APPENDIX I

The fusion protein substrate for TEV in the Example I experiment has the following respective DNA (SEQ ID NO: 3) and protein (SEQ ID NO:4) sequences: His-CBD-TEV protease.

```
SEQ ID NO: 3
ATGAAAATCCATCACCATCATCATCATGGGTCAGGGAGTTCCGGT

TTGACAACGAACCCGGGGGTGAGTGCTTGGCAGGTGAACACAGCG

TACACCGCTGGTCAGCTGGTGACTTACAATGGTAAAACCTACAAA

TGCCTGCAACCACACACTTCACTGGCTGGATGGGAGCCAAGCAAT

GTCCCGGCACTTTGGCAGTTACAGGGGTCTGGTAGCTCGGGAGAA

TCCCTGTTTAAAGGGCCACGTGATTATAACCCGATCTCCTCTAGT

ATATGTCACCTCACAAACGAATCCGATGGACATACCACCAGTCTT

TATGGGATTGGCTTTGGTCCGTTTATAATCACCAACAAACATCTG

TTCCGCCGCAACAATGGGACCCTGGTTGTACAATCACTGCACGGT

GTTTTCAAAGTAAAAGATACGACCACACTGCAGCAGCATTTAGTT

GATGGGCGGGACATGATAATCATTCGCATGCCAAAGGATTTTCCA

CCATTTCCACAGAAACTGAAGTTCCGCGAACCACAACGTGAGGAA

CGCATTTGTCTTGTGACGACTAATTTCCAGACCAAATCAATGAGT

TCTATGGTTAGTGATACCTCGTGTACCTTCCCGAGCGGTGATGGG

ATTTTCTGGAAACATTGGATTCAGACAAAAGATGGACAGTGCGGT

TCCCCGTTGGTATCCACAAGAGACGGTTTTATAGTTGGTATTCAT

TCTGCATCCAATTTTACCAATACAAACAACTACTTCACATCAGTT

CCGAAGAACTTATGGAACTGTTAACTAATCAGGAGGCCCAGCAG

TGGGTATCAGGGTGGCGATTGAACGCCGACAGTGTTCTGTGGGC

GGGCATAAAGTGTTTATGTCTAAACCGGAAGAACCTTTTCAGCCG

GTTAAAGAAGCCACTCAGTTAATGAACTGA
```

-continued

```
The TEV fusion protein (SEQ ID NO: 4 below)
with the recognition and cleavage sites
underlined is:
MKIHHHHHHEEGKLVIWINGDKGYNGLAEVGKKFEKDTGIKVTVE

HPDKLEEKFPQVAATGDGPDIIFWAHDRFGGYAQSGLLAEITPDK

AFQDKLYPFTWDAVRYNGKLIAYPIAVEALSLIYNKDLLPNPPKT

WEEIPALDKELKAKGKSALMFNLQEPYFTWPLIAADGGYAFKYEN

GKYDIKDVGVDNAGAKAGLTFLVDLIKNKHMNADTDYSIAEAAFN

KGETAMTINGPWAWSNIDTSKVNYGVTVLPTFKGQPSKPFVGVLS

AGINAASPNKELAKEFLENYLLTDEGLEAVNKDKPLGAVALKSYE

EELVKDPRIAATMENAQKGEIMPNIPQMSAFWYAVRTAVINAASG

RQTVDEALKDAQTNSSSNNNNNNNNNNNLGENLYFQSMVSKGEELF

TGVVPILVELDGDVNGHKFSVSGEGEGDATYGKLTLKFICTTGKL

PVPWPTLVTTLTYGVQCFSRYPDHMKQHDFFKSAMPEGYVQERTI

FFKDDGNYKTRAEVKFEGDTLVNRIELKGIDFKEDGNILGHKLEY

NYNSHNVYIMADKQKNGIKVNFKIRHNIEDGSVQLADHYQQNTPI

GDGPVLLPDNHYLSTQSALSKDPNEKRDHMVLLEFVTAAGITLGM

DELYK
```

```
After TEV digestion, it separates into
two polypeptides, the first one being
SEQ ID NO: 5:
MKIHHHHHHEEGKLVIWINGDKGYNGLAEVGKKFEKDTGIKVTVE

HPDKLEEKFPQVAATGDGPDIIFWAHDRFGGYAQSGLLAEITPDK

AFQDKLYPFTWDAVRYNGKLIAYPIAVEALSLIYNKDLLPNPPKT

WEEIPALDKELKAKGKSALMFNLQEPYFTWPLIAADGGYAFKYEN

GKYDIKDVGVDNAGAKAGLTFLVDLIKNKHMNADTDYSIAEAAFN

KGETAMTINGPWAWSNIDTSKVNYGVTVLPTFKGQPSKPFVGVLS

AGINAASPNKELAKEFLENYLLTDEGLEAVNKDKPLGAVALKSYE

EELVKDPRIAATMENAQKGEIMPNIPQMSAFWYAVRTAVINAASG

RQTVDEALKDAQTNSSSNNNNNNNNNNNLGENLYFQ
and the second being SEQ ID NO: 6:
SMVSKGEELFTGVVPILVELDGDVNGHKFSVSGEGEGDATYGKLT

LKFICTTGKLPVPWPTLVTTLTYGVQCFSRYPDHMKQHDFFKSAM

PEGYVQERTIFFKDDGNYKTRAEVKFEGDTLVNRIELKGIDFKED

GNILGHKLEYNYNSHNVYIMADKQKNGIKVNFKIRHNIEDGSVQL

ADHYQQNTPIGDGPVLLPDNHYLSTQSALSKDPNEKRDHMVLLEF

VTAAGITLGMDELYK
```

The specific processes, methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein may suitably be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. The invention has been described broadly and generically herein. Each of the narrower species and subgeneric groupings falling within the generic disclosure also form part of the invention.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

---

SEQUENCE LISTING

```
Sequence total quantity: 10
SEQ ID NO: 1              moltype = DNA  length = 930
FEATURE                   Location/Qualifiers
source                    1..930
                          mol_type = genomic DNA
                          organism = Tobacco etch virus
SEQUENCE: 1
atgaaaatcc atcaccatca tcatcatggg tcagggagtt ccggtttgac aacgaacccg   60
ggggtgagtg cttggcaggt gaacacagcg tacaccgctg gtcagctggt gacttacaat  120
ggtaaaacct acaaatgcct gcaaccacac acttcactgg ctggatggga gccaagcaat  180
gtcccggcac tttggcagtt acaggggtct ggtagctcgg gagaatccct gtttaaaggg  240
ccacgtgatt ataacccgat ctcctctagt atatgtcacc tcacaaacga atccgatgga  300
cataccacca gtctttatgg gattggcttt ggtccgttta taatcaccaa caaacatctg  360
ttccgccgca acaatgggac cctggttgta caatcactgc acggtgtttt caaagtaaaa  420
gatacgacca cactgcagca gcatttagtt gatgggcggg acatgataat cattcgcatg  480
ccaaaggatt ttccaccatt tccacagaaa ctgaagttcc gcgaaccaca acgtgaggaa  540
cgcatttgtc ttgtgacgac taatttccag accaaatcaa tgagttctat ggttagtgat  600
acctcgtgta ccttcccgag cggtgatggg attttctgga aacattggat tcagacaaaa  660
gatggacagt gcggttcccc gttggtatcc acaagagacg gtttttatagt tggtattcat  720
tctgcatcca attttaccaa tacaaacaac tacttcacat cagttccgaa gaactttatg  780
gaactgttaa ctaatcagga ggcccagcag tgggtatcag ggtggcgatt gaacgccgac  840
agtgttctgt ggggcgggca taaagtgttt atgtctaaac cggaagaacc ttttcagccg  900
gttaaagaag ccactcagtt aatgaactga                                    930

SEQ ID NO: 2              moltype = AA  length = 309
FEATURE                   Location/Qualifiers
source                    1..309
                          mol_type = protein
                          organism = Tobacco etch virus
SEQUENCE: 2
MKIHHHHHHG SGSSGLTTNP GVSAWQVNTA YTAGQLVTYN GKTYKCLQPH TSLAGWEPSN   60
VPALWQLQGS GSSGESLFKG PRDYNPISSS ICHLTNESDG HTTSLYGIGF GPFIITNKHL  120
FRRNNGTLVV QSLHGVFKVK DTTTLQQHLV DGRDMIIIRM PKDFPPFPQK LKFREPQREE  180
RICLVTTNFQ TKSMSSMVSD TSCTFPSGDG IFWKHWIQTK DGQCGSPLVS TRDGFIVGIH  240
SASNFTNTNN YFTSVPKNFM ELLTNQEAQQ WVSGWRLNAD SVLWGGHKVF MSKPEEPFQP  300
VKEATQLMN                                                          309

SEQ ID NO: 3              moltype = DNA  length = 930
FEATURE                   Location/Qualifiers
source                    1..930
                          mol_type = genomic DNA
                          organism = Tobacco etch virus
SEQUENCE: 3
atgaaaatcc atcaccatca tcatcatggg tcagggagtt ccggtttgac aacgaacccg   60
ggggtgagtg cttggcaggt gaacacagcg tacaccgctg gtcagctggt gacttacaat  120
ggtaaaacct acaaatgcct gcaaccacac acttcactgg ctggatggga gccaagcaat  180
gtcccggcac tttggcagtt acaggggtct ggtagctcgg gagaatccct gtttaaaggg  240
ccacgtgatt ataacccgat ctcctctagt atatgtcacc tcacaaacga atccgatgga  300
cataccacca gtctttatgg gattggcttt ggtccgttta taatcaccaa caaacatctg  360
ttccgccgca acaatgggac cctggttgta caatcactgc acggtgtttt caaagtaaaa  420
gatacgacca cactgcagca gcatttagtt gatgggcggg acatgataat cattcgcatg  480
ccaaaggatt ttccaccatt tccacagaaa ctgaagttcc gcgaaccaca acgtgaggaa  540
```

```
cgcatttgtc ttgtgacgac taatttccag accaaatcaa tgagttctat ggttagtgat    600
acctcgtgta ccttcccgag cggtgatggg attttctgga aacattggat tcagacaaaa    660
gatggacagt gcggttcccc gttggtatcc acaagagacg gttttatagt tggtattcat    720
tctgcatcca attttaccaa tacaaacaac tacttcacat cagttccgaa gaactttatg    780
gaactgttaa ctaatcagga ggcccagcag tgggtatcag ggtggcgatt gaacgccgac    840
agtgttctgt ggggcgggca taaagtgttt atgtctaaac cggaagaacc ttttcagccg    900
gttaaagaag ccactcagtt aatgaactga                                     930
```

```
SEQ ID NO: 4                moltype = AA   length = 635
FEATURE                     Location/Qualifiers
source                      1..635
                            mol_type = protein
                            organism = Tobacco etch virus
SEQUENCE: 4
MKIHHHHHHE EGKLVIWING DKGYNGLAEV GKKFEKDTGI KVTVEHPDKL EEKFPQVAAT    60
GDGPDIIFWA HDRFGGYAQS GLLAEITPDK AFQDKLYPFT WDAVRYNGKL IAYPIAVEAL    120
SLIYNKDLLP NPPKTWEEIP ALDKELKAKG KSALMFNLQE PYFTWPLIAA DGGYAFKYEN    180
GKYDIKDVGV DNAGAKAGLT FLVDLIKNKH MNADTDYSIA EAAFNKGETA MTINGPWAWS    240
NIDTSKVNYG VTVLPTFKGQ PSKPFVGVLS AGINAASPNK ELAKEFLENY LLTDEGLEAV    300
NKDKPLGAVA LKSYEEELVK DPRIAATMEN AQKGEIMPNI PQMSAFWYAV RTAVINAASG    360
RQTVDEALKD AQTNSSSNNN NNNNNNNLGE NLYFQSMVSK GEELFTGVVP ILVELDGDVN    420
GHKFSVSGEG EGDATYGKLT LKFICTTGKL PVPWPTLVTT LTYGVQCFSR YPDHMKQHDF    480
FKSAMPEGYV QERTIFFKDD GNYKTRAEVK FEGDTLVNRI ELKGIDFKED GNILGHKLEY    540
NYNSHNVYIM ADKQKNGIKV NFKIRHNIED GSVQLADHYQ QNTPIGDGPV LLPDNHYLST    600
QSALSKDPNE KRDHMVLLEF VTAAGITLGM DELYK                               635
```

```
SEQ ID NO: 5                moltype = AA   length = 395
FEATURE                     Location/Qualifiers
source                      1..395
                            mol_type = protein
                            organism = Tobacco etch virus
SEQUENCE: 5
MKIHHHHHHE EGKLVIWING DKGYNGLAEV GKKFEKDTGI KVTVEHPDKL EEKFPQVAAT    60
GDGPDIIFWA HDRFGGYAQS GLLAEITPDK AFQDKLYPFT WDAVRYNGKL IAYPIAVEAL    120
SLIYNKDLLP NPPKTWEEIP ALDKELKAKG KSALMFNLQE PYFTWPLIAA DGGYAFKYEN    180
GKYDIKDVGV DNAGAKAGLT FLVDLIKNKH MNADTDYSIA EAAFNKGETA MTINGPWAWS    240
NIDTSKVNYG VTVLPTFKGQ PSKPFVGVLS AGINAASPNK ELAKEFLENY LLTDEGLEAV    300
NKDKPLGAVA LKSYEEELVK DPRIAATMEN AQKGEIMPNI PQMSAFWYAV RTAVINAASG    360
RQTVDEALKD AQTNSSSNNN NNNNNNNLGE NLYFQ                               395
```

```
SEQ ID NO: 6                moltype = AA   length = 240
FEATURE                     Location/Qualifiers
source                      1..240
                            mol_type = protein
                            organism = Tobacco etch virus
SEQUENCE: 6
SMVSKGEELF TGVVPILVEL DGDVNGHKFS VSGEGEGDAT YGKLTLKFIC TTGKLPVPWP    60
TLVTTLTYGV QCFSRYPDHM KQHDFFKSAM PEGYVQERTI FFKDDGNYKT RAEVKFEGDT    120
LVNRIELKGI DFKEDGNILG HKLEYNYNSH NVYIMADKQK NGIKVNFKIR HNIEDGSVQL    180
ADHYQQNTPI GDGPVLLPDN HYLSTQSALS KDPNEKRDHM VLLEFVTAAG ITLGMDELYK    240
```

```
SEQ ID NO: 7                moltype = AA   length = 6
FEATURE                     Location/Qualifiers
source                      1..6
                            mol_type = protein
                            organism = Tobacco etch virus
SEQUENCE: 7
GSGSSG                                                                6
```

```
SEQ ID NO: 8                moltype = AA   length = 7
FEATURE                     Location/Qualifiers
source                      1..7
                            mol_type = protein
                            organism = Tobacco etch virus
SEQUENCE: 8
ENLYFQS                                                               7
```

```
SEQ ID NO: 9                moltype = AA   length = 7
FEATURE                     Location/Qualifiers
source                      1..7
                            mol_type = protein
                            organism = Tobacco etch virus
SEQUENCE: 9
ENLYFQX                                                               7
```

-continued

```
SEQ ID NO: 10          moltype = AA  length = 7
FEATURE                Location/Qualifiers
source                 1..7
                       mol_type = protein
                       organism = Tobacco etch virus
SEQUENCE: 10
ENLYFQM                                                    7
```

What is claimed is:

1. A process of cleaving a target protein with a fusion protein having sequences of Tobacco Etch Virus protease, wild type or mutant, with two affinity tags, and then removing the fusion protein after cleavage by binding to either or both of the affinity tags, comprising:

generating the fusion protein where a chitin binding domain precedes the residues representing the N-terminus of the protease, and the chitin binding domain is preceded by a poly-histidine tag;

combining the fusion protein with a substrate for cleavage by the fusion protein in a reaction solution under reaction conditions; and binding the fusion protein to a solid support having chitin on its support surface or wherein the solid support bears a metal.

2. The process of claim 1 wherein the solid support is a resin or a magnetic bead.

3. The process of claim 2 wherein the magnetic bead includes nickel.

4. The process of claim 2 wherein the solid support is a magnetic bead and further including removing the magnetic beads bearing the bound fusion protein from the reaction solution using magnetic attraction.

5. The process of claim 1 wherein the fusion protein has a series of glycine and serine residues between the poly-histidine tag and the chitin binding domain.

6. The process of claim 5 further including a series of glycine and serine residues between the chitin binding domain and the residues at the N-terminus of the protease.

7. The process of claim 6 wherein the linkers are both 6-mers.

8. The process of claim 6 wherein the linkers are both: GSGSSG (SEQ ID NO: 7).

9. The process of claim 1 wherein the fusion protein includes a MKI leader sequence.

10. A process of cleaving a target protein with a fusion protein having the sequence of SEQ ID NO:2 with two affinity tags, and then removing the fusion protein after cleavage by binding to either or both of the affinity tags, comprising:

combining the fusion protein with a substrate for cleavage by the fusion protein in a reaction solution under reaction conditions; and binding the fusion protein to a solid support having chitin on its support surface or wherein the solid support bears a metal.

11. The process of claim 10 wherein the solid support is a resin or a magnetic bead.

12. The process of claim 11 wherein the magnetic bead includes nickel.

13. The process of claim 11 wherein the solid support is a magnetic bead and further including removing the magnetic beads bearing the bound fusion protein from the reaction solution using magnetic attraction.

* * * * *